United States Patent
Barakat et al.

(10) Patent No.: US 9,527,820 B1
(45) Date of Patent: Dec. 27, 2016

(54) DIETHYLAMMONIUM SALTS OF PHENYL-SUBSTITUTED THIOBARBITURIC ACID AS ANTI-DIABETIC AGENTS

(71) Applicant: KING SAUD UNIVERSITY, Riyadh (SA)

(72) Inventors: Assem Barakat, Riyadh (SA); Mohamed Ali, Riyadh (SA); Abdullah Mohammed Al Majid, Riyadh (SA); Sammer Yousuf, Karachi (PK); Muhammad Iqbal Choudhary, Karachi (PK)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/147,878

(22) Filed: May 5, 2016

(51) Int. Cl.
*A61K 31/515* (2006.01)
*C07D 403/00* (2006.01)
*C07D 239/68* (2006.01)
*C07D 409/14* (2006.01)

(52) U.S. Cl.
CPC ........... *C07D 239/68* (2013.01); *A61K 31/515* (2013.01); *C07D 409/14* (2013.01)

(58) Field of Classification Search
CPC ............................ A61K 31/515; C07D 239/06
USPC .......................................... 514/270; 544/296
See application file for complete search history.

(56) References Cited

U.S. PATENT DOCUMENTS 6,673,925 B2    1/2004    Urwyler et al.

OTHER PUBLICATIONS

Barakat et al., "New Diethyl Ammonium Salt of Thiobarbituric Acid Derivative: Synthesis, Molecular Structure Investigations and Docking Studies," Molecules, 2015, vol. 20, pp. 20642-20658.
V.K. Ahluwalia et al., "Chemistry of Thiobarbituric Acid", Proc. Indian Natn. Sci. Acad., vol. 62 A, No. 5 (1996), pp. 369-413.

*Primary Examiner* — Raymond Henley, III
(74) *Attorney, Agent, or Firm* — Richard C. Litman

(57) ABSTRACT

The diethylammonium salts of phenyl-substituted thiobarbituric acid as anti-diabetic agents include compounds having the formula:

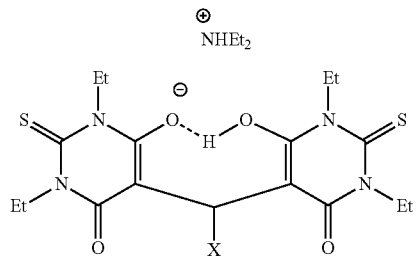

wherein X is:

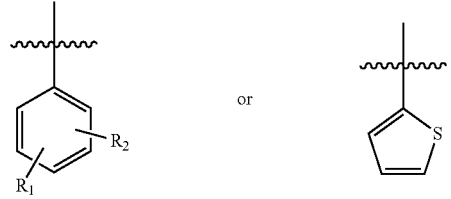

and wherein R1 is selected from the group consisting of a hydrogen, halogen, methyl, trifluoromethyl, methoxy, and nitro, and R2 is either halogen or hydrogen, the $R_1$ and $R_2$ substituents being independently bonded to an ortho-, meta-, or para-carbon of the phenyl substituent.

16 Claims, 11 Drawing Sheets

DIETHYLAMMONIUM SALTS OF PHENYL-SUBSTITUTED THIOBARBITURIC ACID AS ANTI-DIABETIC AGENTS

BACKGROUND OF THE INVENTION

1. Field of the Invention

The present invention relates to anti-diabetic agents, and particularly to diethylammonium salts of phenyl-substituted thiobarbituric acid as anti-diabetic agents.

2. Description of the Related Art

Glucosidase is an enzyme that catalyzes the hydrolysis of polysaccharides into monosaccharides, which may lead to post-prandial hyperglycemia in diabetic patients. The high blood glucose level (hyperglycemia) may cause damage to vital organs, and may lead to complications, such as cataracts, retinopathy, neuropathy, atherosclerosis, nephropathy, and impaired wound healing. Chronic hyperglycemia is also responsible for inducing glycation of different proteins, which may lead to chronic disorders. Inhibition of α-glucosidase is reported to overcome the risk of post-prandial hyperglycemia in diabetic patients, thereby reducing the risk of the above-mentioned health disorders. 1-Deoxynojirimycin, acarbose, miglitol, etc. have been developed as α-glucosidase inhibitors. However, many of these inhibitors have adverse effects and low patient tolerance. Therefore, it would be desirable to provide safe and effective α-glucosidase inhibitors to control diabetic and cardiovascular complications due to hyperglycemia.

Thus, diethylammonium salts of phenyl-substituted thiobarbituric acid as anti-diabetic agents solving the aforementioned problems is desired.

SUMMARY OF THE INVENTION

The diethylammonium salts of phenyl-substituted thiobarbituric acid as anti-diabetic agents includes compounds having the formula:

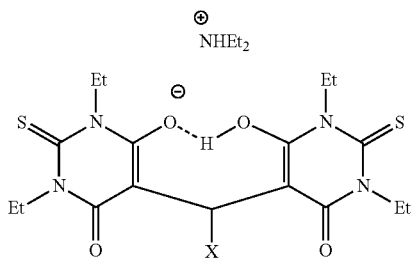

wherein X is:

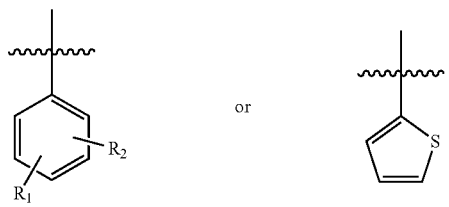

and wherein R1 is selected from the group consisting of a hydrogen, halogen, methyl, trifluoromethyl, methoxy, and nitro, and R2 is either halogen or hydrogen, the $R_1$ and $R_2$ substituents being independently bonded to an ortho-, meta-, or para-carbon of the phenyl substituent.

A method for preparing the diethylammonium salts includes: mixing 1,3-diethyl-2-thioxodihydropyrimidine-4,6(1H,5H)-dione (also called 2-thiobarbituric acid) with diethylamine and benzaldehyde functionalized with the desired substituent (a benzaldehyde derivative) in water while stirring at room temperature for up to five hours. The diethylammonium salt precipitates from the mixture, and may be filtered and washed with petroleum ether or other suitable organic solvent.

An effective amount of the diethylammonium salt may be administered to a diabetic patient in need thereof for inhibiting the activity of α-glucosidase, thereby reducing the risk of complications resulting from post-prandial hyperglycemia.

These and other features of the present invention will become readily apparent upon further review of the following specification

BRIEF DESCRIPTION OF THE DRAWINGS

FIG. 3 shows the $^1$H-NMR spectrum of compound 3a

FIG. 4 shows the $^{13}$C-NMR spectrum of compound 3a.

Similar reference characters denote corresponding features consistently throughout the attached drawings.

DETAILED DESCRIPTION OF THE PREFERRED EMBODIMENTS

The diethylammonium salts of phenyl-substituted thiobarbituric acid as anti-diabetic agents includes compounds having the formula:

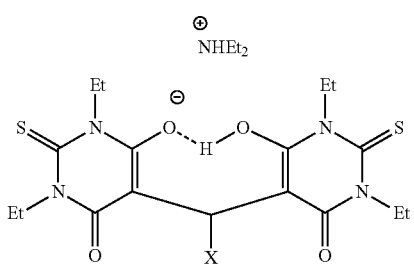

wherein X is:

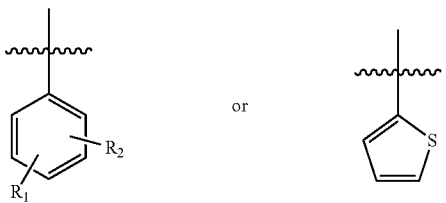

and wherein R1 is selected from the group consisting of a hydrogen, halogen, methyl, trifluoromethyl, methoxy, and nitro, and R2 is either halogen or hydrogen, the $R_1$ and $R_2$ substituents being independently bonded to an ortho-, meta-, or para-carbon of the phenyl substituent.

The diethylammonium salt can be formulated as a pharmaceutical composition comprising the diethylammonium salts as an active agent and a pharmaceutically acceptable carrier, diluent or excipient. A method for treating diabetes can comprise the step of administering to a patient in need thereof a therapeutically effective amount of the pharmaceutical composition comprising the diethylammonium salts. The compound can be in an "effective amount" to elicit the biological or medical response of a tissue, system, animal or human that is being sought by the researcher, veterinarian, medical doctor or other clinician. As would be understood by those skilled in the art of treating diabetes, the term "treatment" does not necessarily mean that the hyperglycemia is completely cured. The term "treatment" encompasses any inhibition of hyperglycemia and associated diabetic and cardiovascular complications.

Figure 1:
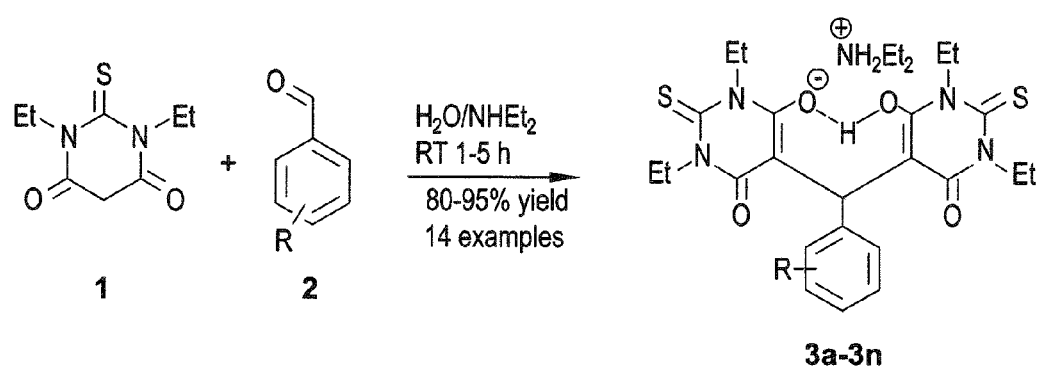
FIG. 1 is a reaction scheme for the synthesis of diethylammonium salts of phenyl-substituted thiobarbituric acid according to the present invention.

The anti-diabetic compounds can be synthesized based on an aldol condensation-Michael addition reaction in one-pot strategy, as illustrated in FIG. 1., which includes mixing 1,3-diethyl-2-thioxodihydropyrimidine-4,6(1H,5H)-dione (also called 2-thiobarbituric acid) 1 with diethylamine and benzaldehyde functionalized with the desired substituent 2 while stirring at room temperature for up to five hours to obtain the diethylammonium salt product 3a to 3n. The method can further comprise filtering the precipitated diethylammonium salt product and washing it with petroleum ether. Typically, a ratio of the concentration of 2-thiobarbituric acid with substituted benzaldehyde and ethyl amine is 2:1:1, respectively. This protocol is generally straightforward, environmentally benign and efficient.

The benzaldehyde compound can include unsubstituted benzaldehyde, 4-chlorobenzaldehyde, 2,4-dichlorobenzaldehyde, 2,6-dichlorobenzaldehyde, 4-bromobenzaldehyde, 4-fluorobenzaldehyde, 3-bromobenzaldehyde, 3-methylbenzaldehyde, 4-methylbenzaldehyde, 4-(trifluoromethyl)benzaldehyde, 4-nitrobenzaldehyde, 3-nitrobenzaldehyde or 4-anisaldehyde. However other benzaldehyde compounds could be chosen as desired to improve the potency as an anti-diabetic inhibitor.

The diethylammonium salts of phenyl-substituted thiobarbituric acid in this disclosure can include the following compounds: 5-((1,3-diethyl-6-hydroxy-4-oxo-2-thioxo-1,2,3,4-tetrahydropyrimidin-5-yl)(phenyl)methyl)-1,3-diethyl-6-oxo-2-thioxo-1,2,3,6-tetrahydropyrimidin-4-olate, diethylammonium 5-((4-chlorophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate, diethylammonium 5-((1,3-diethyl-6-hydroxy-4-oxo-2-thioxo-1,2,3,4-tetrahydropyrimidin-5-yl)(p-tolyl)methyl)-1,3-diethyl-6-oxo-2-thioxo-1,2,3,6-tetrahydropyrimidin-4-olate, diethylammonium 5-((4-bromophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate, diethylammonium 5-((3-bromophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate, diethylammonium 5-((1,3-diethyl-6-hydroxy-4-oxo-2-thioxo-1,2,3,4-tetrahydropyrimidin-5-yl)(m-tolyl)methyl)-1,3-diethyl-6-oxo-2-thioxo-1,2,3,6-tetrahydropyrimidin-4-olate, diethylammonium 5-((1,3-diethyl-6-hydroxy-4-oxo-2-thioxo-1,2,3,4-tetrahydropyrimidin-5-yl)(4-nitrophenyl)methyl)-1,3-diethyl-6-oxo-2-thioxo-1,2,3,6-tetrahydropyrimidin-4-olate, diethylammonium 5-((1,3-diethyl-6-hydroxy-4-oxo-2-thioxo-1,2,3,4-tetrahydropyrimidin-5-yl)(3-nitrophenyl)methyl)-1,3-diethyl-6-oxo-2-thioxo-1,2,3,6-tetrahydropyrimidin-4-olate, diethylammonium 5-((2,4-dichlorophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate, diethylammonium 5-((2,6-dichlorophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate, diethylammonium 5-((1,3-diethyl-6-hydroxy-4-oxo-2-thioxo-1,2,3,4-tetrahydropyrimidin-5-yl)(thiophen-2-yl)methyl)-1,3-diethyl-6-oxo-2-thioxo-1,2,3,6-tetrahydropyrimidin-4-olate, diethylammonium 5-((1,3-diethyl-6-hydroxy-4-oxo-2-thioxo-1,2,3,4-tetrahydropyrimidin-5-yl)(4-methoxyphenyl)methyl)-1,3-diethyl-6-oxo-2-thioxo-1,2,3,6-tetrahydropyrimidin-4-olate, diethylammonium 5-((1,3-diethyl-6-hydroxy-4-oxo-2-thioxo-1,2,3,4-tetrahydropyrimidin-5-yl)(4-fluorophenyl)methyl)-1,3-diethyl-6-oxo-2-thioxo-1,2,3,6-tetrahydropyrimidin-4-olate, and diethylammonium 5-((1,3-diethyl-6-hydroxy-4-oxo-2-thioxo-1,2,3,4-tetrahydropyrimidin-5-yl)(4-(trifluoromethyl)phenyl)methyl)-1,3-diethyl-6-oxo-2-thioxo-1,2,3,6-tetrahydropyrimidin-4-olate.

The present teachings will be understood more readily by reference to the following examples, which are provided by way of illustration.

Example 1

Synthesis of Diethylammonium Salts of 2-Thiobarbituric Acid Via Aldol Condensation-Michael Addition (General Method 1)

A mixture of 1 (3 mmol) and aldehyde 2 (1.5 mmol), as well as $Et_2NH$ (1 Equiv.) were placed in 3 mL of $H_2O$. The reaction mixture was kept at room temperature up to 5 h under stirring. After completion of the reaction, monitored by TLC, the solid product was filtered, washed with petroleum ether, and the final products obtained without any further purification 3a-n.

Example 2

Synthesis of Compound 3a

Diethylammonium 5-((1,3-diethyl-6-hydroxy-4-oxo-2-thioxo-1,2,3,4-tetrahydropyrimidin-5-yl)(phenyl)methyl)-1,3-diethyl-6-oxo-2-thioxo-1,2,3,6-tetrahydropyrimidin-4-olate (3a)

Figure 3:
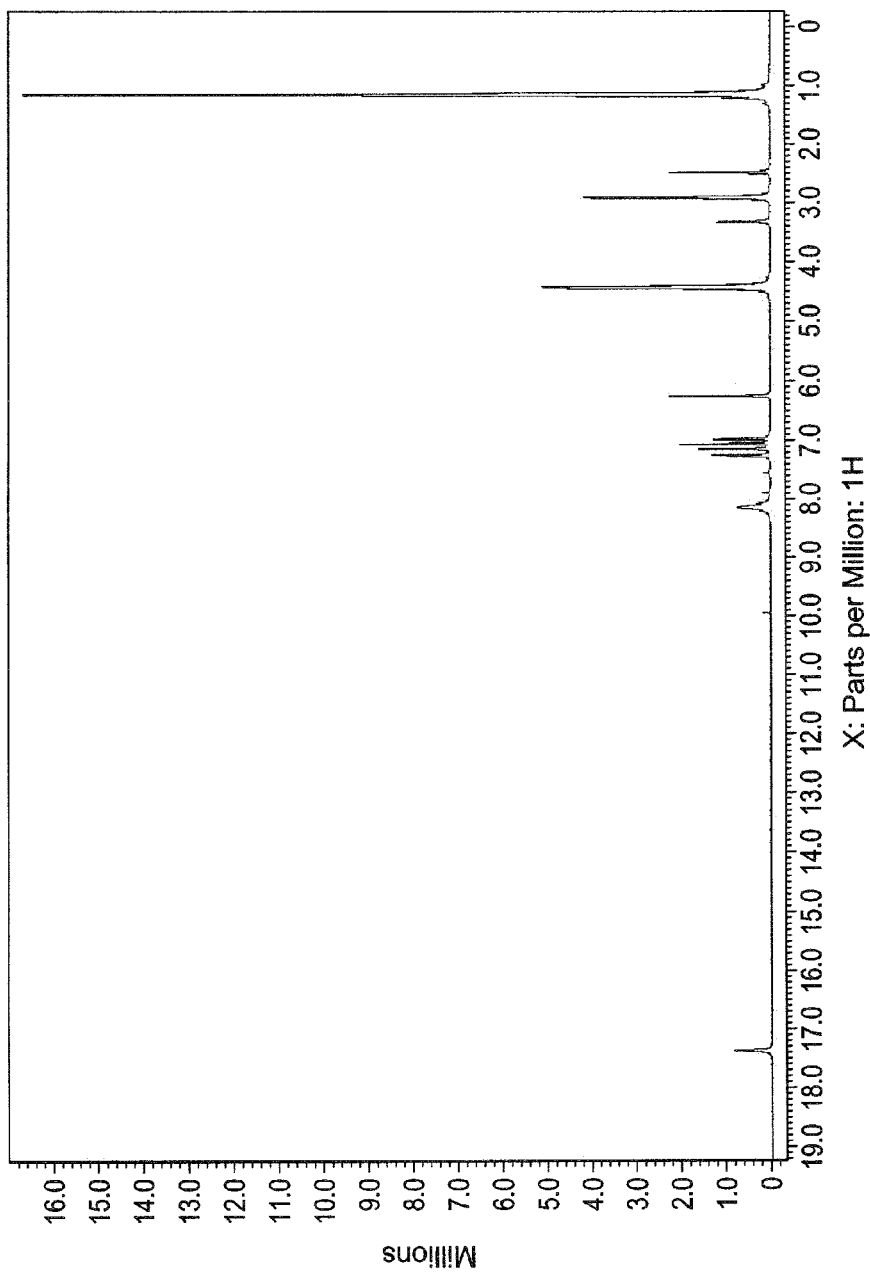
Figure 4:
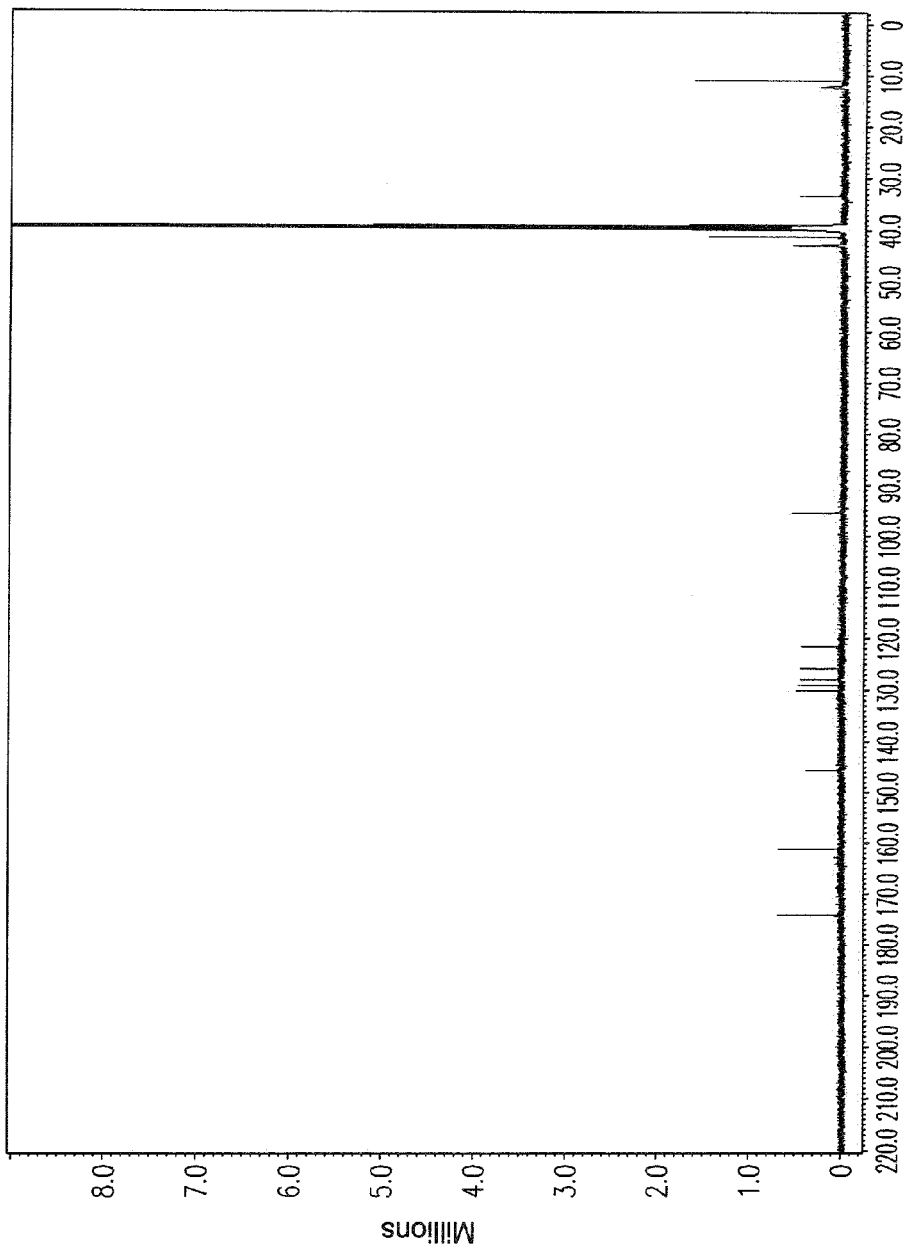
Figure 5A:
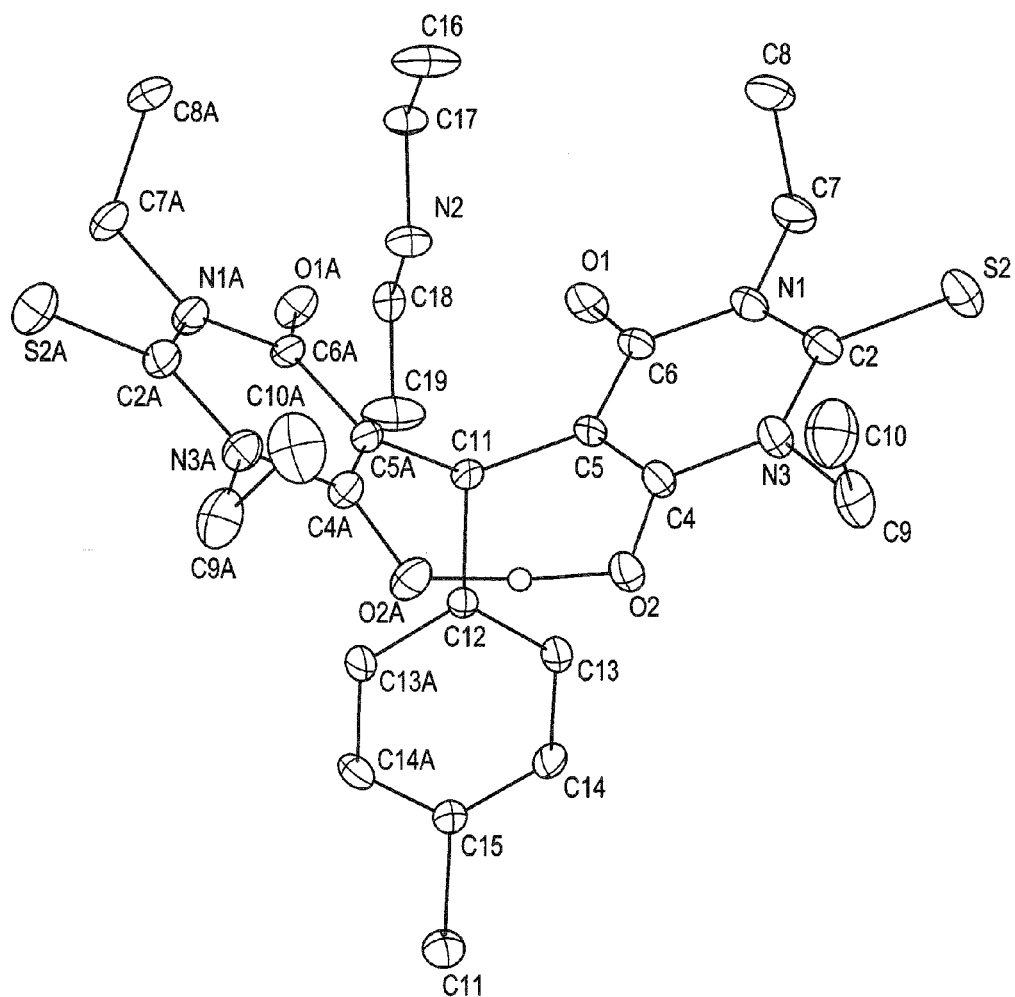
FIG. 5A is an Oak Ridge Thermal Ellipsoid Plot (ORTEP) drawing of compound 3b.
Figure 5B:
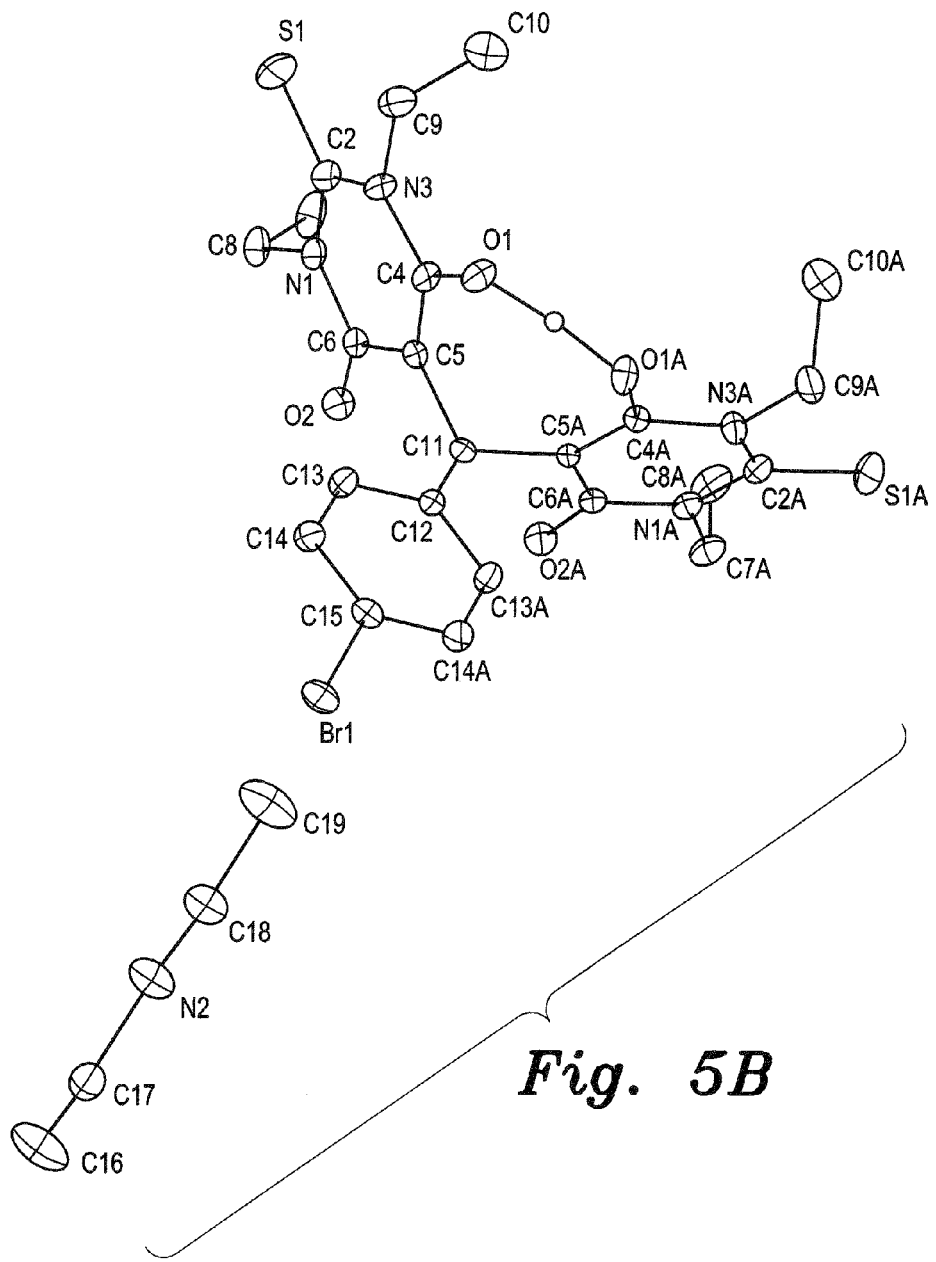
FIG. 5B is an Oak Ridge Thermal Ellipsoid Plot (ORTEP) drawing of compound 3d.
Figure 5C:
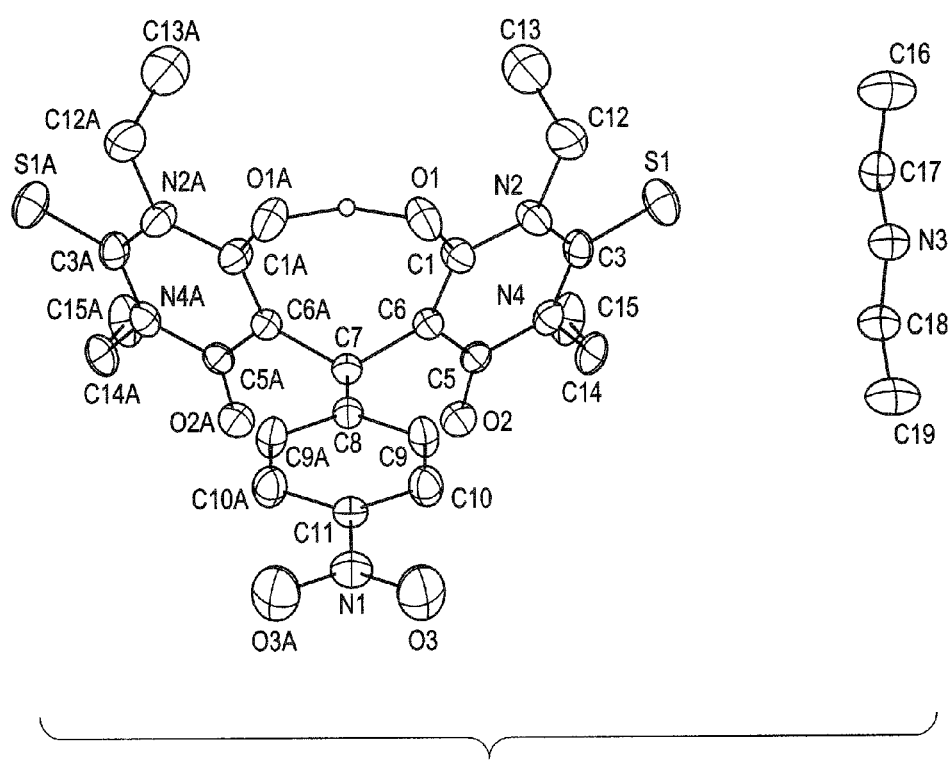
FIG. 5C is an ORTEP drawing of compound 3g.
Figure 5D:
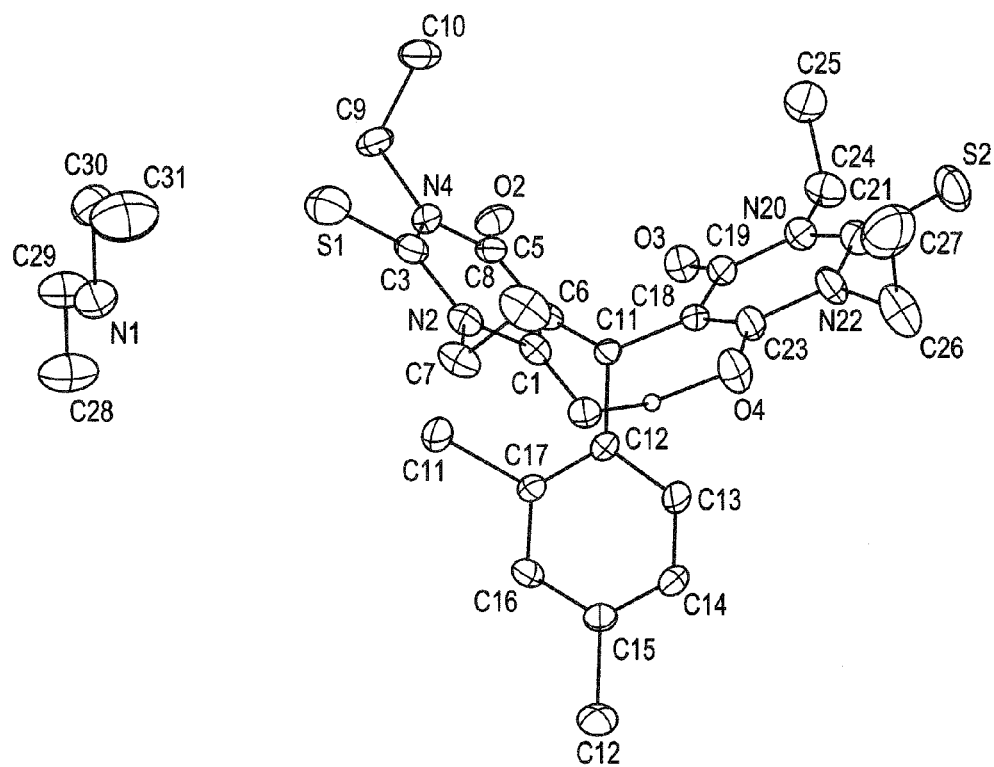
FIG. 5D is an ORTEP drawing of compound 3i.
Figure 5E:
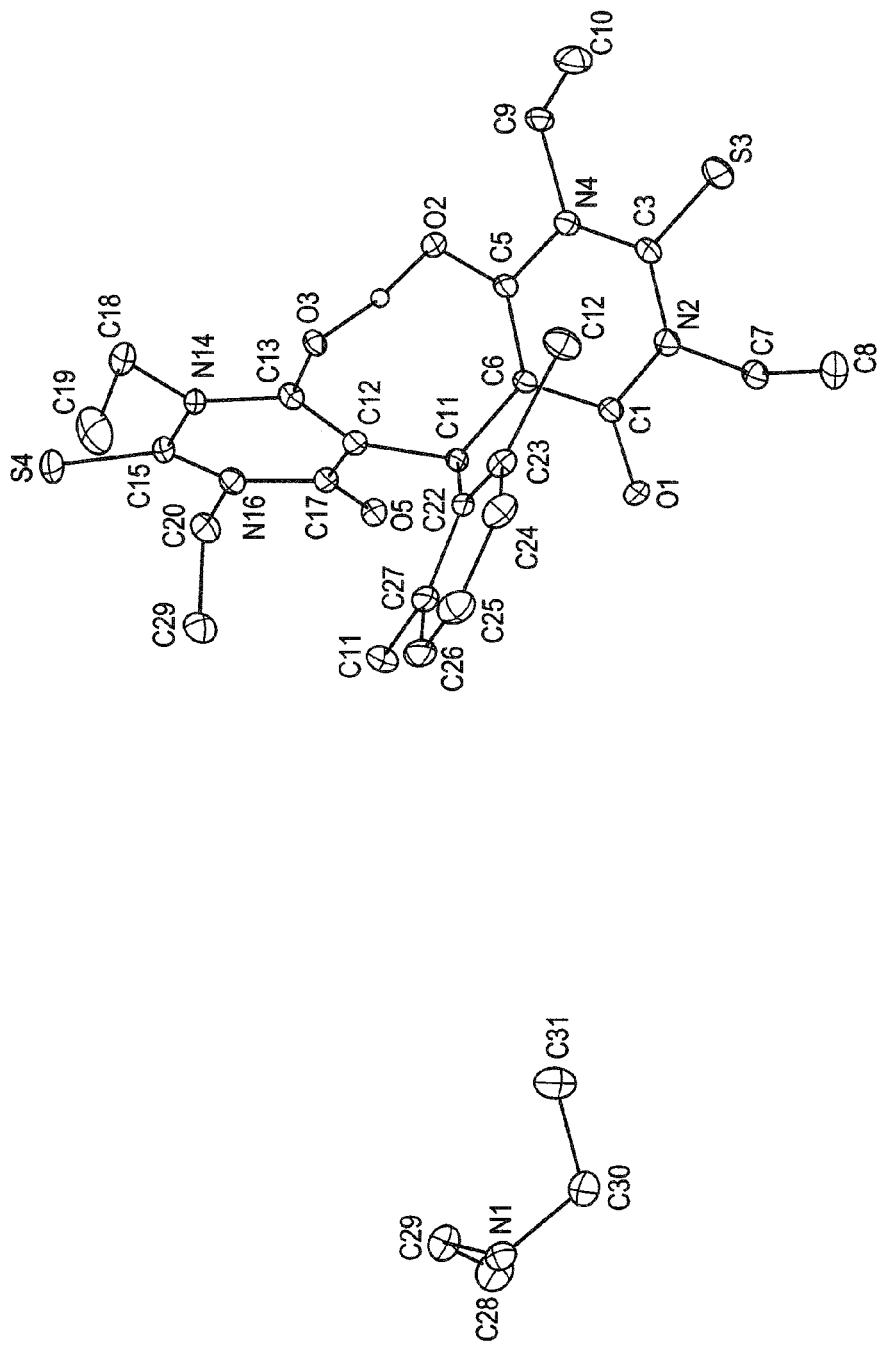
FIG. 5E is an ORTEP drawing of compound 3j.

Pure product 3a was obtained according to the method of Example 1 as a white material. m.p. 185° C.; (2.85 mmol, 95%, 1.6 g). IR (KBr): 2976, 2936, 2872, 1644, 1613, 1575, 1424, 1383, 1262 cm$^{-1}$; $^1$H-NMR (DMSO-d$_6$, 400 MHz) 17.49 (s, 1H, OH), 8.16 (bs, 2H, NH$_2$Et$_2$), 7.18-6.96 (m, 5H, Ph), 6.28 (s, 1H, PhCH), 4.45 (q, 8H, J=7.3 Hz, CH$_2$CH$_3$), 2.95 (q, 4H, J=7.3 Hz, NH$_2$CH$_2$CH$_3$), 1.15 (t, 18H, J=7.3 Hz, CH$_2$CH$_3$); $^{13}$C-NMR (100 MHz, DMSO-d$_6$): δ=174.6, 161.8, 143.0, 128.4, 126.9, 125.5, 96.7, 42.0, 41.6, 31.5, 13.0, 12.7, 11.6; Anal. for C$_{27}$H$_{39}$N$_5$O$_4$S$_2$; Calcd: C, 57.73; H, 7.00; N, 12.47; S, 11.42. Found: C, 57.74; H, 7.01; N, 12.48; S, 11.41; LC/MS (ESI):m/z=562.76 [M]$^+$. FIGS. 3-4 are representative $^1$H and $^{13}$C NMR of compound 3a.

Example 3

Synthesis of Compound 3b

Diethylammonium 5-((4-chlorophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate (3b)

Pure product 3b was obtained according to the method of Example 1 as a white powder. m.p. 209° C.; (2.82 mmol, 94%, 1.68 g). IR (KBr): 2978, 2932, 2872, 1644, 1582, 1486, 1428, 1385, 1297, 1266 cm$^{-1}$; $^1$H-NMR (DMSO-d$_6$, 400 MHz) 17.41 (s, 1H, OH), 8.17 (bs, 2H, NH$_2$Et$_2$), 7.24 (d, 2H, J=7.3 Hz, Ph), 7.03 (d, 2H, J=7.3 Hz, Ph), 6.24 (s, 1H, PhCH), 4.44 (q, 8H, J=7.3 Hz, CH$_2$CH$_3$), 2.92 (q, 4H, J=7.3 Hz, NH$_2$CH$_2$CH$_3$), 1.15 (t, 18H, J=7.3 Hz, CH$_2$CH$_3$); $^{13}$C-NMR (100 MHz, DMSO-d$_6$): δ=174.7, 161.7, 142.2, 130.0, 128.9, 128.3, 96.4, 42.3, 41.5, 32.0, 13.0, 11.6; Anal. for C$_{27}$H$_{38}$ClN$_5$O$_4$S$_2$; Calcd: C, 54.39; H, 6.42; Cl, 5.95; N, 11.75; S, 10.76. Found: C, 54.40; H, 6.41; Cl, 5.97; N, 11.73; S, 10.74; LC/MS (ESI): m/z=596.20 [M]$^+$.

Example 4

Synthesis of Compound 3c

Diethylammonium 5-((1,3-diethyl-6-hydroxy-4-oxo-2-thioxo-1,2,3,4-tetrahydropyrimidin-5-yl)(p-tolyl)methyl)-1,3-diethyl-6-oxo-2-thioxo-1,2,3,6-tetrahydropyrimidin-4-olate (3c)

Pure product 3c was obtained according to the method of Example 1 as a white powder. m.p. 185° C.; (2.79 mmol, 93%, 1.66 g). IR (KBr): 2978, 2932, 2872, 1604, 1582, 1428, 1384, 1370, 11296, 1266 cm$^{-1}$; $^1$H-NMR (DMSO-d$_6$, 400 MHz) 17.41 (s, 1H, OH), 8.17 (bs, 2H, NH$_2$Et$_2$), 6.98 (d, 2H, J=7.3 Hz, Ph), 6.83 (d, 2H, J=7.3 Hz, Ph), 6.21 (s, 1H, PhCH), 4.45 (q, 8H, J=7.3 Hz, CH$_2$CH$_3$), 2.95 (q, 4H, J=7.3 Hz, NH$_2$CH$_2$CH$_3$), 2.21 (s, 3H, CH$_3$), 1.15 (t, 18H, J=7.3 Hz, CH$_2$CH$_3$); $^{13}$C-NMR (100 MHz, DMSO-d$_6$): δ=174.6, 161.7, 139.8, 134.2, 128.9, 126.8 96.8, 41.7, 41.5, 31.3, 21.0, 13.0, 12.7, 11.6; Anal. for C$_{28}$H$_{41}$N$_5$O$_4$S$_2$; Calcd: C, 58.41; H, 7.18; N, 12.16; S, 11.14. Found: C, 58.43; H, 7.19; N, 12.14; S, 11.15; LC/MS (ESI): m/z=596.20 [M]$^+$.

Example 5

Synthesis of Compound 3d

Diethylammonium 5-((4-bromophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate (3d)

Pure product 3d was obtained according to the method of Example 1 as a white powder. m.p. 200° C.; (2.82 mmol, 94%, 1.8 g). IR (KBr): 2978, 2931, 2871, 1643, 1585, 1482, 1428, 384, 1296, 1267 cm$^{-1}$; $^1$H-NMR (DMSO-d$_6$, 400 MHz) 17.38 (s, 1H, OH), 8.14 (bs, 2H, NH$_2$Et$_2$), 7.35 (d, 2H, J=7.3 Hz, Ph), 6.92 (d, 2H, J=7.3 Hz, Ph), 6.20 (s, 1H, PhCH), 4.42 (q, 8H, J=7.3 Hz, CH$_2$CH$_3$), 2.92 (q, 4H, J=7.3 Hz, NH$_2$CH$_2$CH$_3$), 1.14 (t, 18H, J=7.3 Hz, CH$_2$CH$_3$); $^{13}$C-NMR (100 MHz, DMSO-d$_6$): δ=174.13, 161.1, 142.0, 130.6, 128.7, 117.8, 95.7, 442.0, 41.5, 31.5, 13.5, 11.0; Anal. For C$_{27}$H$_{38}$BrN$_5$O$_4$S$_2$; Calcd: C, 50.62; H, 5.98; Br, 12.47; N, 10.93; S, 10.01. Found: C, 50.61; H, 5.98; Br, 12.46; N, 10.95; S, 10.00; LC/MS (ESI): m/z=641.66 [M]$^+$.

Example 6

Synthesis of Compound 3e

Diethylammonium 5-((3-bromophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate (3e)

Pure product 3e was obtained according to the method of Example 1 as a white powder. m.p. 197° C.; (2.73 mmol, 91%, 1.74 g). IR (KBr): 2979, 2929, 1603, 1584, 1531, 1423, 1381, 1346, 1294, 1263 cm$^{-1}$; $^1$H-NMR (DMSO-d$_6$, 400 MHz) 17.40 (s, 1H, OH), 8.15 (bs, 2H, NH$_2$Et$_2$), 7.26 (d, 1H, J=7.3 Hz, Ph), 7.07 (s, 1H, Ph), 6.97 (d, 1H, J=7.3 Hz, Ph), 6.26 (s, 1H, PhCH), 4.44 (q, 8H, J=7.3 Hz, CH$_2$CH$_3$), 2.92 (q, 4H, J=7.3 Hz, NH$_2$CH$_2$CH$_3$), 1.14 (t, 18H, J=7.3 Hz, CH$_2$CH$_3$); $^{13}$C-NMR (100 MHz, DMSO-d$_6$): δ=174.2, 161.1, 145.6, 130.1, 129.0, 127.9, 125.6, 121.3, 95.6, 42.0, 41.5, 31.3, 13.2, 11.0; Anal. for C$_{27}$H$_{38}$BrN$_5$O$_4$S$_2$; Calcd: C, 50.62; H, 5.98; Br, 12.47; N, 10.93; O, 9.99; S, 10.01. Found: C, 50.63; H, 5.98; Br, 12.48; N, 10.95; S, 10.03; LC/MS (ESI): m/z=641.66 [M]$^+$.

Example 7

Synthesis of Compound 3f

Diethylammonium 5-((1,3-diethyl-6-hydroxy-4-oxo-2-thioxo-1,2,3,4-tetrahydropyrimidin-5-yl)(m-tolyl)methyl)-1,3-diethyl-6-oxo-2-thioxo-1,2,3,6-tetrahydropyrimidin-4-olate (3f)

Pure product 3f was obtained according to the method of Example 1 as a white powder. m.p. 190° C.; (2.76 mmol, 92%, 1.59 g,). IR (KBr): 2977, 2931, 1605, 1421, 1406, 1380, 1338, 1294, 1263 cm$^{-1}$; $^1$H-NMR (DMSO-d$_6$, 400 MHz) 17.46 (s, 1H, OH), 8.15 (bs, 2H, NH$_2$Et$_2$), 7.04 (d, 1H, J=7.3 Hz, Ph), 6.97 (d, 1H, J=7.3 Hz, Ph), 6.76 (s, 1H, Ph), 6.22 (s, 1H, PhCH), 4.44 (q, 8H, J=7.3 Hz, CH$_2$CH$_3$), 2.90 (q, 4H, J=7.3 Hz, NH$_2$CH$_2$CH$_3$), 2.18 (s, 3H, CH$_3$), 1.14 (t, 18H, J=7.3 Hz, CH$_2$CH$_3$); $^{13}$C-NMR (100 MHz, DMSO-d$_6$): δ=174.0, 161.5, 142.4, 136.4, 127.6, 126.9, 125.6, 123.6, 96.1, 41.9, 14.3, 31.4, 21.3, 13.1, 11.0; Anal. for C$_{28}$H$_{41}$N$_5$O$_4$S$_2$; Calcd: C, 58.41; H, 7.18; N, 12.16; S, 11.14. Found: C, 58.40; H, 7.19; N, 12.17; S, 11.13; LC/MS (ESI): m/z=575.79 [M]$^+$.

Example 8

Synthesis of Compound 3g

Diethylammonium 5-((1,3-diethyl-6-hydroxy-4-oxo-2-thioxo-1,2,3,4-tetrahydropyrimidin-5-yl)(4-nitrophenyl)methyl)-1,3-diethyl-6-oxo-2-thioxo-1,2,3,6-tetrahydropyrimidin-4-olate (3g)

Pure product 3g was obtained according to the method of Example 1 as a white powder. m.p. 195° C.; (2.7 mmol, 90%, 1.64 g). IR (KBr): 2978, 2930, 1684, 1596, 1482, 1482, 1429, 1384, 1371, 1294, 1270, 1270 cm$^{-1}$; $^1$H-NMR (DMSO-d$_6$, 400 MHz) 17.32 (s, 1H, OH), 8.15 (bs, 2H, NH$_2$Et$_2$), 8.11 (d, 2H, J=7.3 Hz, Ph), 7.24 (d, 2H, J=7.3 Hz, Ph), 6.35 (s, 1H, PhCH), 4.44 (q, 8H, J=7.3 Hz, CH$_2$CH$_3$), 2.92 (q, 4H, J=7.3 Hz, NH$_2$CH$_2$CH$_3$), 1.13 (t, 18H, J=7.3 Hz, CH$_2$CH$_3$); $^{13}$C-NMR (100 MHz, DMSO-d$_6$): δ=174.3, 161.1, 151.6, 145.3, 127.7, 123.2, 123.2, 95.5, 42.1, 41.5, 31.8, 12.3, 11.0; Anal. for C$_{27}$H$_{38}$N$_6$O$_6$S$_2$; Calcd: C, 53.45; H, 6.31; N, 13.85; S, 10.57. Found: C, 53.44; H, 6.32; N, 13.86; S, 10.56; LC/MS (ESI): m/z=607.23 [M]$^+$.

Example 9

Synthesis of Compound 3h

Diethylammonium 5-((1,3-diethyl-6-hydroxy-4-oxo-2-thioxo-1,2,3,4-tetrahydropyrimidin-5-yl)(3-nitrophenyl)methyl)-1,3-diethyl-6-oxo-2-thioxo-1,2,3,6-tetrahydropyrimidin-4-olate (3h)

Pure product 3h was obtained according to the method of Example 1 as a white powder. m.p. 185° C.; (2.64 mmol, 88%, 1.6 g). IR (KBr): 2980, 2928, 1637, 1583, 1531, 1293, 1264 cm$^{-1}$; $^1$H-NMR (DMSO-d$_6$, 400 MHz) 17.38 (s, 1H, OH), 8.13 (bs, 2H, NH$_2$Et$_2$), 7.96 (d, 2H, J=7.3 Hz, Ph), 7.76 (s, 1H, Ph), 7.48 (t, 1H, J=7.3 Hz, Ph), 6.36 (s, 1H, PhCH), 4.44 (q, 8H, J=7.3 Hz, CH$_2$CH$_3$), 2.92 (q, 4H, J=7.3 Hz, NH$_2$CH$_2$CH$_3$), 1.14 (t, 18H, J=7.3 Hz, CH$_2$CH$_3$); $^{13}$C-NMR (100 MHz, DMSO-d$_6$): δ=174.3, 161.1, 147.7, 145.2, 133.6, 129.5, 120.5, 95.4, 42.1, 41.5, 31.2, 12.3, 11.0; Anal for C$_{27}$H$_{38}$N$_6$O$_6$S$_2$; Calcd: C, 53.45; H, 6.31; N, 13.85; S, 10.57. Found: C, 53.46; H, 6.33; N, 13.84; S, 10.60; LC/MS (ESI): m/z=575.79 [M]$^+$.

Example 10

Synthesis of Compound 3i

Diethylammonium 5-((2,4-dichlorophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate (3i)

Pure product 3i was obtained according to the method of Example 1 as a colorless crystal. m.p. 185° C.; (2.55 mmol, 85%, 1.60 g,). IR (KBr): 2977, 2935, 28827, 1684, 1597, 1428, 1385, 1296, 1271 cm$^{-1}$; $^1$H-NMR (DMSO-d$_6$, 400 MHz) 17.38 (s, 1H, OH), 8.13 (bs, 2H, NH$_2$Et$_2$), 7.37 (d, 1H, J=7.3 Hz, Ph), 7.24 (s, 1H, Ph), 7.18 (d, 1H, J=7.3 Hz, Ph), 6.05 (s, 1H, PhCH), 4.40 (q, 8H, J=7.3 Hz, CH$_2$CH$_3$), 2.91 (q, 4H, J=7.3 Hz, NH$_2$CH$_2$CH$_3$), 1.12 (t, 18H, J=7.3 Hz, CH$_2$CH$_3$); $^{13}$C-NMR (100 MHz, DMSO-d$_6$): δ=174.2, 160.9, 139.8, 133.4, 131.3, 130.7, 128.8, 126.3, 94.9, 42.0, 41.5, 31.3, 12.3, 11.1; Anal. for C$_{27}$H$_{37}$Cl$_2$N$_5$O$_4$S$_2$; Calcd: C, 51.42; H, 5.91; Cl, 11.24; N, 11.10; S, 10.17. Found: C, 51.41; H, 5.91; Cl, 11.25; N, 11.11; S, 10.17; LC/MS (ESI): m/z=631.65 [M]$^+$.

Example 11

Synthesis of Compound 3j

Diethylammonium 5-((2,6-dichlorophenyl)(1,3-diethyl-6-hydroxy-4-oxo-2-thioxo-1,2,3,4-tetrahydropyrimidin-5-yl)methyl)-1,3-diethyl-6-oxo-2-thioxo-1,2,3,6-tetrahydropyrimidin-4-olate (3j)

Pure product 3j was obtained according to the method of Example 1 as a colorless crystal. m.p. 185° C.; (2.4 mmol, 80%, 1.51 g). IR (KBr): 2981, 2935, 2871, 1708, 1679, 1591, 1430, 1339, 1294, 1267 cm$^{-1}$; $^1$H-NMR (DMSO-d$_6$, 400 MHz) 17.38 (s, 1H, OH), 8.15 (bs, 2H, NH$_2$Et$_2$), 7.23 (d, 2H, J=7.3 Hz, Ph), 7.09 (t, 1H, J=7.3 Hz, Ph), 6.11 (s, 1H, PhCH), 4.38 (q, 8H, J=7.3 Hz, CH$_2$CH$_3$), 2.92 (q, 4H, J=7.3 Hz, NH$_2$CH$_2$CH$_3$), 1.12 (t, 18H, J=7.3 Hz, CH$_2$CH$_3$); $^{13}$C-NMR (100 MHz, DMSO-d$_6$): δ=173.9, 160.9, 139.8, 133.4, 131.3, 130.7, 128.8, 126.3, 94.9, 42.0, 41.5, 31.2, 12.2, 11.0; Anal. for C$_2$H$_{37}$Cl$_2$N$_5$O$_4$S$_2$; Calcd: C, 51.42; H, 5.91; Cl, 11.24; N, 11.10; S, 10.17. Found: C, 51.43; H, 5.90; Cl, 11.22; N, 11.08; S, 10.18; LC/MS (ESI): m/z=631.65 [M]$^+$.

Example 12

Synthesis of Compound 3k

Diethylammonium 5-((1,3-diethyl-6-hydroxy-4-oxo-2-thioxo-1,2,3,4-tetrahydropyrimidin-5-yl)(thiophen-2-yl)methyl)-1,3-diethyl-6-oxo-2-thioxo-1,2,3,6-tetrahydropyrimidin-4-olate (3k).

Pure product 3j was obtained according to the method of Example 1 as a yellow powder. m.p. 175° C.; (2.76 mmol, 90%, 1.53 g). IR (KBr): 2977, 2936, 1645, 1580, 1440, 1367, 1339, 1265 cm$^{-1}$; $^1$H-NMR (DMSO-d$_6$, 400 MHz) 17.74 (s, 1H, OH), 8.15 (bs, 2H, NH$_2$Et$_2$), 7.14 (d, H, J=5.1 Hz, Ph), 6.78 (d, 1H, J=5.1 Hz, Ph), 6.47 (d, 1H, J=5.1 Hz, Ph), 6.25 (s, 1H, PhCH), 4.43 (q, 8H, J=7.3 Hz, CH$_2$CH$_3$), 2.90 (q, 4H, J=7.3 Hz, NH$_2$CH$_2$CH$_3$), 1.14 (t, 18H, J=7.3 Hz, CH$_2$CH$_3$); $^{13}$C-NMR (100 MHz, DMSO-d$_6$): δ=174.2, 160.9, 122.8, 122.7, 96.6, 42.0, 41.5, 31.2, 12.2, 11.0; Anal. for C$_{25}$H$_{37}$N$_5$O$_4$S$_3$; Calcd: C, 52.88; H, 6.57; N, 12.33; S, 16.94. Found: C, 52.90; H, 6.58; N, 12.34; S, 16.94; LC/MS (ESI): m/z=568.79 [M]$^+$.

Example 13

Synthesis of Compound 3l

Diethylammonium 5-((1,3-diethyl-6-hydroxy-4-oxo-2-thioxo-1,2,3,4-tetrahydropyrimidin-5-yl)(4-methoxyphenyl)methyl)-1,3-diethyl-6-oxo-2-thioxo-1,2,3,6-tetrahydropyrimidin-4-olate (3l)

Pure product 3l was obtained according to the method of Example 1 as a yellow powder. m.p. 175° C.; (2.64 mmol, 88%, 1.56 g). IR (KBr): 3442, 2978, 2933, 2871, 2835, 1726, 1616, 1508, 1435, 1269 cm$^{-1}$; $^1$H-NMR (DMSO-d$_6$, 400 MHz) 17.50 (s, 1H, OH), 8.17 (bs, 2H, NH$_2$Et$_2$), 6.89 (d, 2H, J=5.1 Hz, Ph), 6.76 (d, 2H, J=5.1 Hz, Ph), 6.21 (s, 1H, PhCH), 4.45 (q, 8H, J=7.3 Hz, CH$_2$CH$_3$), 3.86 (s, 3H, CH$_3$), 2.93 (q, 4H, J=7.3 Hz, NH$_2$CH$_2$CH$_3$), 1.15 (t, 18H, J=7.3 Hz, CH$_2$CH$_3$); $^{13}$C-NMR (100 MHz, DMSO-d$_6$): δ=174.0, 161.2, 134.1, 127.3, 113.2, 96.3, 54.8, 41.4, 31.5, 12.5, 12.1, 11.0; Anal. for C$_{28}$H$_{41}$N$_5$O$_5$S$_2$; Calcd: C, 56.83; H, 6.98; N, 11.83; S, 10.83. Found: C, 56.83; H, 6.99; N, 11.85; S, 10.81; LC/MS (ESI): m/z=591.79 [M]$^+$.

Example 14

Synthesis of Compound 3m

Diethylammonium 5-((1,3-diethyl-6-hydroxy-4-oxo-2-thioxo-1,2,3,4-tetrahydropyrimidin-5-yl)(4-fluorophenyl)methyl)-1,3-diethyl-6-oxo-2-thioxo-1,2,3,6-tetrahydropyrimidin-4-olate (3m)

Pure product 3m was obtained according to the method of Example 1 as a white powder. m.p. 190° C.; (2.79 mmol, 93%, 1.61 g). IR (KBr): 3447, 2980, 2931, 2871, 1615, 1502, 1431, 1386, 1345, 1268 cm$^{-1}$; $^1$H-NMR (DMSO-d$_6$, 400 MHz) 17.50 (s, 1H, OH), 8.15 (bs, 2H, NH$_2$Et$_2$), 6.98 (m, 4H, Ph), 6.23 (s, 1H, PhCH), 4.43 (q, 8H, J=7.3 Hz, CH$_2$CH$_3$), 2.92 (q, 4H, J=7.3 Hz, NH$_2$CH$_2$CH$_3$), 1.14 (t, 18H, J=7.3 Hz, CH$_2$CH$_3$); $^{13}$C-NMR (100 MHz, DMSO-d$_6$): δ=174.1, 161.3, 161.1, 138.3, 128.1, 128.0, 114.5, 114.2, 96.0, 41.4, 31.4, 12.42, 11.0; Anal. for C$_{27}$H$_{38}$FN$_5$O$_4$S$_2$; Calcd: C, 55.94; H, 6.61; F, 3.28; N, 12.08; S, 11.06. Found: C, 55.93; H, 6.60; F, 3.29; N, 12.10; S, 11.05; LC/MS (ESI): m/z=579.75 [M]$^+$.

Example 15

Synthesis of Compound 3n

Diethylammonium 5-((1,3-diethyl-6-hydroxy-4-oxo-2-thioxo-1,2,3,4-tetrahydropyrimidin-5-yl)(4-(trifluoromethyl)phenyl)methyl)-1,3-diethyl-6-oxo-2-thioxo-1,2,3,6-tetrahydropyrimidin-4-olate (3n)

Pure product 3n was obtained according to the method of Example 1 as a white powder. m.p. 183° C.; (2.76 mmol, 92%, 1.73 g). IR (KBr): 3440, 2982, 2930, 1680, 1620, 1500, 1430, 1340, 1260 cm$^{-1}$; $^1$H-NMR (DMSO-d$_6$, 400 MHz) 17.34 (s, 1H, OH), 8.15 (bs, 2H, NH$_2$Et$_2$), 7.55 (d, 2H, J=5.1 Hz, Ph), 7.19 (d, 2H, J=5.1 Hz, Ph), 6.32 (s, 1H, PhCH), 4.43 (q, 8H, J=7.3 Hz, CH$_2$CH$_3$), 2.92 (q, 4H, J=7.3 Hz, NH$_2$CH$_2$CH$_3$), 1.14 (t, 18H, J=7.3 Hz, CH$_2$CH$_3$); $^{13}$C-NMR (100 MHz, DMSO-d$_6$): δ=175.1, 161.3, 161.1, 138.3, 128.1, 128.0, 114.5, 114.2, 96.0, 41.4, 32.0, 12.4, 11.0; Anal. for C$_{28}$H$_{38}$F$_3$N$_5$O$_4$S$_2$; Calcd: C, 53.40; H, 6.08; F, 9.05; N, 11.12; S, 10.18. Found: C, 53.41; H, 6.07; F, 9.05; N, 11.15; S, 10.20; LC/MS (ESI): m/z=629.76 [M]$^+$.

Figure 2A:
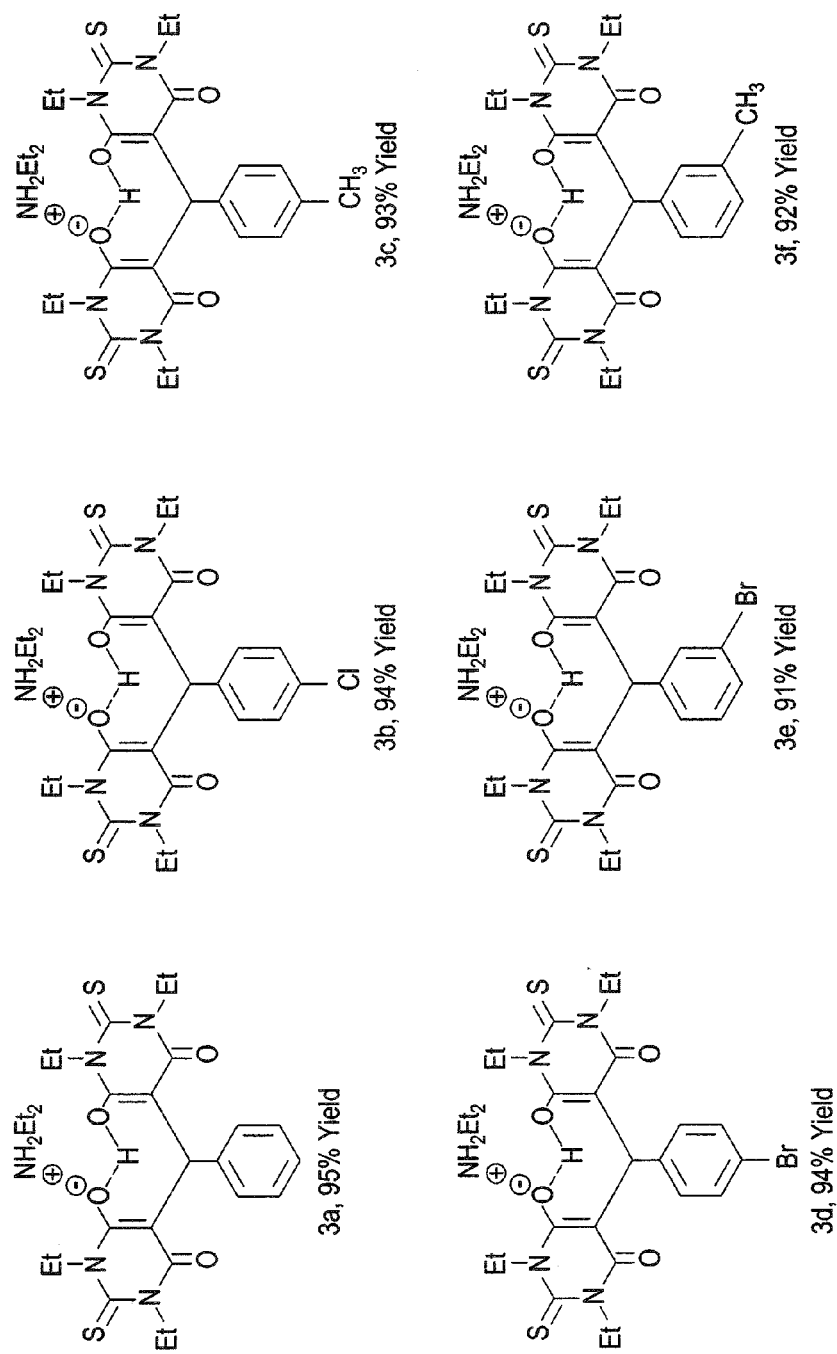
FIG. 2A is the structural formula of six of the diethylammonium salts of phenyl-substituted thiobarbituric acid according to the present invention, designated as compounds 3a through 3f, respectively.
Figure 2B:
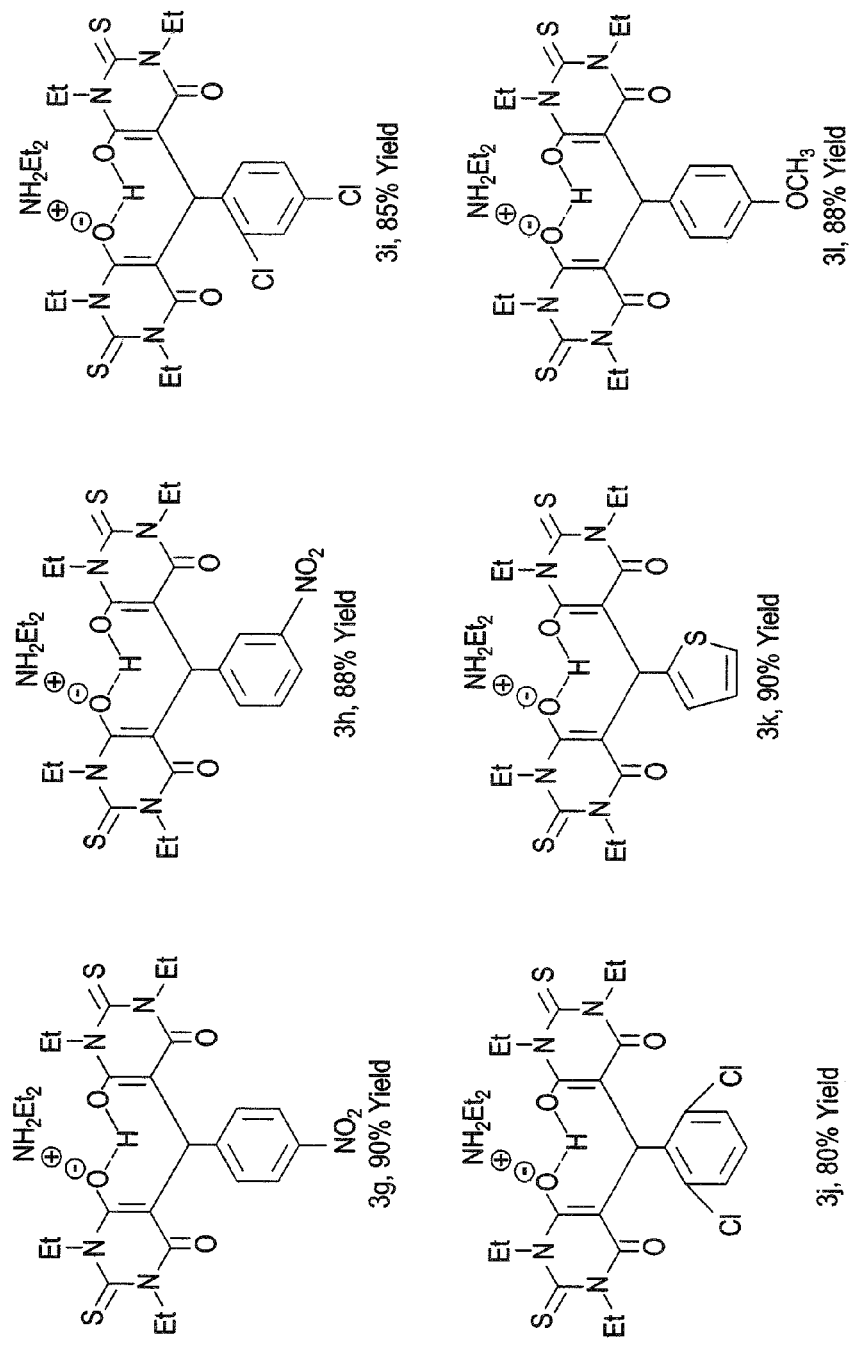
FIG. 2B is the structural formula of another six diethylammonium salts of phenyl-substituted thiobarbituric acid according to the present invention, designated as compounds 3g through 3l, respectively.
Figure 2C:
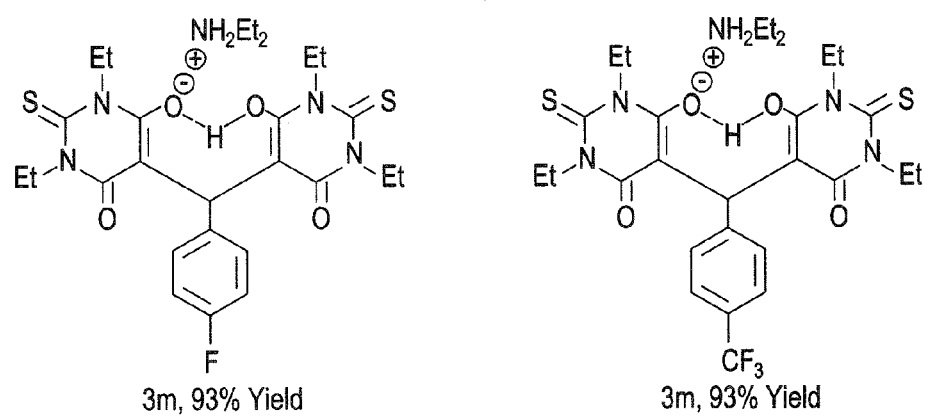
FIG. 2C is the structural formula of another two diethylammonium salts of phenyl-substituted thiobarbituric acid according to the present invention, designated as compounds 3m and 3n, respectively.

As illustrated in FIG. 1, a green protocol one pot multi component reaction was employed to obtain the diethylammonium salts of phenyl-substituted thiobarbituric acid 3a-n in very good to excellent yields. In the present investigation, reaction of thiobarbituric acid 1 (2 equiv.) with substitute benzaldehyde 2 (1 equiv.) in the presence of aqueous diethylamine (Et2NH) medium at room temperature afforded target compounds 3a-n in quantitative yields by simple filtration. Fourteen derivatives were prepared. The chemical structures of the products 3a-n (shown in FIGS. 2A, 2B, and 2C) were elucidated by using spectroscopic techniques, including $^1$H-NMR, $^{13}$C-NMR, IR, and MS. Furthermore, the following compounds 3b, 3d, 3g, 3i, and 3j were solved by X-ray single crystal, as shown in the ORTEP diagrams of FIGS. 5A-5E, respectively.

The synthesized compounds 3a-n were evaluated for their in vitro α-glucosidase enzyme inhibition activity. All the members of the series (3a-n) exhibited a potent α-glucosidase inhibition, with IC$_{50}$ values 415.8±4.0, 39.3±0.62, 199.8±8.7, 26.8±0.17, 31.5±0.16, 308.8±6.3, 219.1±8.4, 42.9±0.57, 19.4±1.84, 162.2±6.2, 101.8±2.0 μM, 210.9±10, 51.7±2.2, and 163.8±4.5, respectively. All tested compounds were found to be more active than the standard drug, acarbose (IC$_{50}$=840±1.73 μM). Compound 3a, having a phenyl ring attached to the central thiobarbiturate skeleton, was found to be the least active member of the series, with an IC$_{50}$ value 415.8±4.0 μM. However, the activity increased when the phenyl ring was substituted with a chlorine atom at the para position, as observed in compound 3b (IC$_{50}$=415.8±4.0 μM). Further increase in activity was observed for compound 3i (IC$_{50}$=19.4±1.84 μM), having an ortho- and para-dicholoro-substituted phenyl ring, instead of a single para-substituted benzene ring. The positions of chloro group also apparently contribute towards the activity of thiobabiturates. This observation was further supported by decreased activity of a dichloro ortho-substituted phenyl ring, compound 3j (IC$_{50}$=162.2±6.2 μM), as compared to the ortho- and para-substituted dicholoro phenyl ring, compound 3i (IC$_{50}$=19.4±1.84 μM), the most potent member of the series. However, this pattern was not very prominent in the case of the para- and ortho-substituted bromo phenyl ring, compounds 3d (IC$_{50}$=26.8±0.17 μM) and 3e (IC$_{50}$=31.5±0.16 μM), respectively. Para-substituted fluorine was also investigated. In the case of para-substituted fluoro phenyl ring, compound 3m, the IC$_{50}$ value was 51.7±2.2 μM, but the activity decreased in the case of the trifluoromethyl phenyl ring, compound 3n (IC$_{50}$=163.8±4.5 μM). Similarly, the para-methyl phenyl (toluene) ring, compound 3e (IC$_{50}$=199.8±8.7 μM), was found to be more active than meta-substituted-methyl phenyl (toluene) ring, compound 3f (IC$_{50}$=308.8±6.3 μM).

The presence of a strong electron withdrawing group on the phenyl ring was found to increase the α-glucusidase inhibitory activity, as observed for compounds 3g (IC$_{50}$=219.1±8.4 μM) and 3h (IC$_{50}$=42.9±0.57 μM) having para- and meta-substituted nitro phenyl rings attached to the central thiobarbiturate moiety. The comparison of activities of 3g (IC$_{50}$=219.1±8.4 μM), 3l (IC$_{50}$=210.9±10 μM), and 3h (IC$_{50}$=42.9±0.57 μM) further supported the inference that the position of the substituent on the phenyl ring attached to the central thiobarbiturate moiety greatly influences the activities of the various compounds. Detailed studies are required on these large libraries in order to unambiguously identify the structural features that may be responsible of activity. The α-glucosidase inhibition results are summarized in Table 1.

TABLE 1

| α-Glucosidase Inhibition activity | |
| --- | --- |
| Compound | α-Glucosidase Inhibition (IC$_{50}$ in μM) |
| 3a | 415.8 ± 4.0 |
| 3b | 39.3 ± 0.62 |
| 3c | 199.8 ± 8.7 |
| 3d | 26.8 ± 0.17 |
| 3e | 31.5 ± 0.16 |
| 3f | 308.8 ± 6.3 |
| 3g | 219.1 ± 8.4 |
| 3h | 42.9 ± 0.57 |
| 3i | 19.4 ± 1.84 |
| 3j | 162.2 ± 6.2 |
| 3k | 101.8 ± 2.0 |
| 3l | 210.9 ± 10 |
| 3m | 51.7 ± 2.2 |
| 3n | 163.8 ± 4.5 |
| Std. Acarbose | 840 ± 1.73 |

SEM = Standard error of mean

As demonstrated above, a series of α-glucosidase inhibitors incorporating diethylammonium salts of phenyl-substituted thiobarbituric acid (3a-3n) were prepared in good to excellent chemical yields. These compounds (3a-3n) were identified as potent α-glucosidase enzyme inhibitors. All of these compounds were found to be several folds more active than the standard drug acarbose in in vitro biochemical studies. The potent α-glucosidase inhibiting activities of these compounds indicate their future potential applications as possible drug candidates for the treatment of hyperglycemia and associated diabetic and cardiovascular complications.

It is to be understood that the present invention is not limited to the embodiments described above, but encompasses any and all embodiments within the scope of the following claims.

We claim:

1. A diethylammonium salt of phenyl-substituted thiobarbituric acid, comprising a compound having the formula:

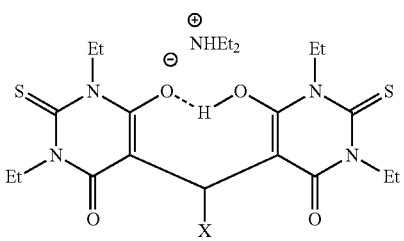

wherein X is:

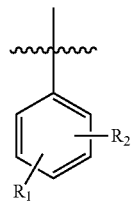

and wherein R1 is selected from the group consisting of a hydrogen, halogen, methyl, trifluoromethyl, methoxy, and nitro, and R2 is either halogen or hydrogen, the $R_1$ and $R_2$ substituents being independently bonded to an ortho-, meta-, or para-carbon of the phenyl substituent.

2. A pharmaceutical composition, comprising a compound according to claim 1 and a pharmaceutically acceptable carrier, excipient or diluent.

3. A method for treating diabetes, comprising the step of administering to a diabetic patient in need thereof an effective amount of a compound according to claim 1 for inhibiting post-prandial hyperglycemia.

4. A method of making the diethylammonium salt of phenyl-substituted thiobarbituric acid of claim 1, comprising the step of mixing 2-thiobarbituric acid with diethylamine and substituted or unsubstituted benzaldehyde in water in order to precipitate the diethylammonium salt.

5. The method of making the diethylammonium salt of phenyl-substituted thiobarbituric acid according to claim 4, further comprising the step of stirring the mixture at room temperature for up to five hours to ensure complete precipitation.

6. The method of making the diethylammonium salt of phenyl-substituted thiobarbituric acid according to claim 4, further comprising the step of filtering the mixture to recover the precipitated diethylammonium salt.

7. The method of making the diethylammonium salt of phenyl-substituted thiobarbituric acid according to claim 6, further comprising the step of washing the recovered precipitate with petroleum ether.

8. The diethylammonium salt of phenyl-substituted thiobarbituric acid according to claim 1, wherein R1 and R2 are both hydrogen.

9. The diethylammonium salt of phenyl-substituted thiobarbituric acid according to claim 1, wherein R1 is chlorine and R2 is hydrogen.

10. The diethylammonium salt of phenyl-substituted thiobarbituric acid according to claim 1, wherein R1 and R2 are both chlorine.

11. The diethylammonium salt of phenyl-substituted thiobarbituric acid according to claim 1, wherein R1 is $NO_2$ and R2 is hydrogen.

12. The diethylammonium salt of phenyl-substituted thiobarbituric acid according to claim 1, wherein R1 is methyl and R2 is hydrogen.

13. The diethylammonium salt of phenyl-substituted thiobarbituric acid according to claim 1, wherein R1 is $OCH_3$ and R2 is hydrogen.

14. The diethylammonium salt of phenyl-substituted thiobarbituric acid according to claim 1, wherein R1 is bromine and R2 is hydrogen.

15. The diethylammonium salt of phenyl-substituted thiobarbituric acid according to claim 1, wherein R1 is fluorine and R2 is hydrogen.

16. The diethylammonium salt of phenyl-substituted thiobarbituric acid according to claim 1, wherein R1 is $CF_3$ and R2 is hydrogen.

* * * * *